United States Patent [19]

Gasseling et al.

[11] Patent Number: 4,906,472
[45] Date of Patent: Mar. 6, 1990

[54] PELLETIZED RODENTICIDE FROM RODENT TOXIC PLANT MATTER

[75] Inventors: Thomas Gasseling; Lana Landis, both of Yakima, Wash.

[73] Assignee: John I. Haas, Inc., Yakima, Wash.

[21] Appl. No.: 331,677

[22] Filed: Mar. 30, 1989

[51] Int. Cl.$^4$ .................... A01N 65/00; A01N 25/08; A01N 25/00

[52] U.S. Cl. ........................ 424/405; 424/84; 424/195.1; 424/410; 424/409; 424/DIG. 8

[58] Field of Search ...................... 424/84, 195.1, 410, 424/DIG. 8, 405, 409

[56] References Cited

U.S. PATENT DOCUMENTS

| | | | |
|---|---|---|---|
| 1,952,977 | 3/1934 | Edmonds | 42/195.1 |
| 2,590,536 | 9/1945 | Heal | 424/195.1 |
| 3,321,364 | 5/1967 | Kessler | 424/195.1 |
| 3,544,677 | 12/1970 | Lapham et al. | 424/84 |
| 3,816,610 | 6/1974 | Lusby | 424/84 |
| 4,246,001 | 1/1981 | Bauman | 44/62 |
| 4,287,183 | 9/1981 | Hagerman et al. | 424/84 |
| 4,313,011 | 4/1982 | Weil et al. | 585/408 |
| 4,581,378 | 4/1986 | Lazar et al. | 424/84 |

OTHER PUBLICATIONS

"Testing for Tumor Promoters in Euphorbia Lathyris: Analysis of Possible Health Hazards", by Bissell, Nemethy, Riddle, and Calvin, *Bulletin of Environmental Contamination and Toxicology*, vol. 27, pp. 894–902, 1981.

"Safe Homegrown Pesticides" by Diane Downs, *Mother Earth*, Jul./Aug. 1986, pp. 29–30, 32.

"Euphorbia Lathyris", author and publication source unknown (apparently from an old pharmacopia type publication).

"Energy Potential of Leafy Spurge (*Euphorbia esula*)", by Maxwell, Wiatr, and Fay, *Economic Botany*, 39 (2), 1985, 1 page.

"The Desert: An Age Old Challenge Grows", *National Geographic*, vol. 156, No. 5, Nov. 1979, p. 617.

"Energy Farmers: Growing Tommorrow's Fuel", by Peter Ognibene, *Science Digest*, Aug. 1981, pp. 98–100.

"Whole-Plant Oils, Potential New Industrial Raw Materials", by Buchanan, Otey, Russell, and Cull, *Journal of the American Oil Chemists' Society*, vol. 55, pp. 657–662, Sep. 1978.

"Cocarcinogenic Principles from the Seed Oil of 'Croton tiglium' and from Other Euphorbiaceae", by Erich Hecker, *Cancer Research*, vol. 28, pp. 2338–2348, Nov. 1968.

*National Geographic*, Feb. 1981, p. 91.

"Oil From Plants", by Melvin Calvin, Department of Chemistry and Lawrence Berkeley Laboratory, University of California, Berkeley, Calif., Jan. 1983, pp. 1–22.

"New Toxic, Irritant and Cocarcinogenic Diterprene Esters from Euphorbiaceae and from Thymelaeceae", by Erich Hecker, *Pure and Appl. Chem.*, vol. 49, pp. 1423–1431, 1977.

"Structure Determination of the New Tetracyclic Diterpene Ingenol-Triacetate with Triple Product Methods", by Zechmeister, Brandl and Hoppe, *Letters*, No. 47, pp. 4075–4078, 1970.

*Primary Examiner*—Joseph L. Schofer
*Assistant Examiner*—Carmen B. Pili-Curtis
*Attorney, Agent, or Firm*—Patrick M. Dwyer; David L. Garrison

[57] ABSTRACT

A rodenticide composition of pelletized rodent toxic plant materials such as a *Euphorbia lathyrus* and methods of rodent control employing pelletized *Euphorbia lathyrus*.

8 Claims, No Drawings

PELLETIZED RODENTICIDE FROM RODENT TOXIC PLANT MATTER

TECHNICAL FIELD

This invention relates to new rodenticide compositions. In particular, this invention relates to a pelletized rodenticide made from materials of a plant having known rodent toxic constituents. More particularly, the invention relates to a rodenticide comprised of pelletized Euphorbia lathyrus, a method of preparing a pelletized rodenticide from plant matter, and a method of controlling rodents with the pelletized rodenticide.

BACKGROUND INFORMATION

It is well known that the control of rodents, such as gophers, mice, rabbits, and the like, is of widespread concern throughout the agricultural industry, and the commercial search for an efficient and effective rodenticide continues. See Lazar et al. (1986) U.S. Pat. No. 4,581,378. Large scale commercial agricultural ventures require in addition a high degree of cost effectiveness.

However, the general direction of the search appears to be in the area of modifying food substances, typically grain materials, so that they become toxic to rodents while at the same time remaining attractive to them. For example, see Lapham et al. (1970) U.S. Pat. No. 3,544,677 and Hagerman et al. (1981) U.S. Pat. No. 4,287,183, as well as Lazar et al. cited above. Even Lusby (1974) U.S. Pat. No. 3,816,610, suggests the use of a conventional rodent attracting food substance such as grain or dried blood in his otherwise unconventional method.

No known rodenticide makes use of rodent toxic plant materials in a distributable form as the primary ingredient of a rodenticide composition. Edmonds (1934) U.S. Pat. No. 1,952,977, discloses the rodenticidal use of an extract of the plant Red Squill. However Edmonds' disclosed method of use of the extract as a rodenticide requires that it be mixed a substantial quantity of some rodent edible food such as bread or toast. Even the extracted Red Squill plant material which is disclosed by Edmonds for possible use as a rodenticide after it is dried, apparently requires a greater than 50% by weight admixture of molasses in order to be attractive to rodents. Neither is it known to make a pelletized rodenticide exclusively, or nearly exclusively, from rodent toxic plant materials.

Accordingly it is an object of the invention to provide a distributable rodenticide in pelletized form which consists primarily or exclusively of rodent toxic plant materials with only a small percentage by weight, if any, of rodent attracting substances.

In addition to Red Squill, Euphorbia lathyrus, also known as Caper Spurge and as Nature's Farewell, has high concentrations of rodent toxic substances. It is a fairly easy to grow and inexpensively produced and harvested weed-like plant. The Euphorbia lathyrus plant is relatively prolific in diverse growing environments and, when planted as a hedge around small home gardens, has been reported to serve as an effective rodent deterrent on this limited scale. It appears to do so in this limited application because the roots spread out beneath the growing Euphorbia plants and interlock with the roots of adjacent Euphorbia plants when they are planted closely enough together (the root radius growing to some 2 feet in a mature plant). Burrowing rodents who desire to enter gardens surrounded by such Euphorbia lathyrus hedges must ordinarily burrow into and through the root fibers of the Euphorbia lathyrus plant, necessarily ingesting some of the toxic root fibers. The rodents are thereby either discouraged from further burrowing or are killed by the toxic effect of the milky white latex-like substance present in the root fibers. The same milky white toxic substance exists throughout the Euphorbia lathyrus plant including the above ground portions of the plant, such as the stems and leaves, and is particularly concentrated in the seeds. However it is not known that rodents will attempt to consume any portion of a Euphorbia lathyrus plant, except for fortuitous ingestion of root fibers which happen to be in their way as they burrow from one location to another. Therefore there has been no suggestion in the art that Euphorbia lathyrus might serve as a distributable rodenticide.

It is therefore a further object of the invention to provide a distributable rodenticide in the form of chopped and pelletized plant materials from the Euphorbia lathyrus plant.

It is another object of the invention to provide a method of preparing a pelletized rodenticide from rodent toxic plant materials, and a method of controlling rodents with the pelletized rodenticide.

DISCLOSURE OF THE INVENTION

The above objects and others which will become apparent to those skilled in the art are accomplished by the means and in the manner set forth herein. As rodenticide preparations in the past have been concerned with making toxic an ordinary rodent food substance, while at the same time maintaining a high level of attractiveness of the poisoned food to the rodent, many drawbacks and disadvantages have appeared which are not present if the rodent can be induced to eat plant materials which are already naturally toxic to the rodent. For example, the sweeteners commonly added to make poisoned rodent food attractive lead to deterioration of the product, both on the shelf and in the field, so that the poisoned product looses attractiveness over time. Another drawback is the complexity and expense of proper formulation, preparation, packaging, and distribution of conventional rodenticides.

Moreover, conventional rodenticides with their often high level of broad spectrum attractants, such as sweeteners, are a decided hazard to domestic animals that are equally attracted to the sweetness. An ideal commercial, especially agricultural, rodenticide would attract only rodents and would repel domestic animals. It would be inexpensive in both materials and preparation and it would be highly effective in toxicity/deterrence.

A rodent toxic plant material which can be simply and inexpensively harvested, chopped, and pelletized eliminates these drawbacks because a rodent can be induced to eat the pelletized toxic plant materials while domestic animals cannot. When pelletized to contain a high percentage by weight of plant material with little or no added attractants, such a composition is of no interest to domestic animals, but will be eaten by hungry foraging rodents. The method of pelletizing chopped toxic plant materials is simple and cost effective because it employs conventional pelletizing equipment such as is employed for alfalfa and hops.

The invention therefore comprises a distributable pelletized rodenticide preferably made exclusively of rodent toxic plant materials. A preferred embodiment would make use of the Euphorbia lathyrus plant. However, other rodent toxic plants may be employed, and the toxic plant materials need not be the exclusive ingredients. It is contemplated that other toxic plants may be employed, and that compositions will be employed which are not exclusively Euphorbia lathyrus. The invention also comprises a method of preparing the rodenticide, and of controlling rodents with the pelletized rodenticide. The Euphorbia lathyrus pellets contain little or no attractant additives to deteriorate with time. The pellets do not contain added poisons and therefore give no telltale scent. Domestic animals are not attracted and appear to avoid the pellets. Yet the starving rodent who will voraciously attack the bark and roots of orchard plantings and other crops will consume enough of the pellets to die.

Because agricultural control of rodents is most necessary in those places and during those seasons, such as winter, when the rodents are otherwise starving and are in full foraging and scavenging mode of feeding, the not unnatural appearing pellets are accepted, at least on trial, as a food source. In application the pellets are made far more readily available to the scavenging rodent than the agricultural product to be protected. Thus for example, in winter when orchards typically suffer heavy rodent damage, pelletized toxic plant materials are scattered around the roots of the trees of the orchard, and the scavenging rodents ingest enough of the pellets to die, or at least be discouraged from returning.

BEST MODE FOR CARRYING OUT THE INVENTION

The Euphorbia lathyrus plant is preferred as the plant material from which the rodenticide pellets are made. However it is contemplated that other plant materials which are rodent toxic and relatively rodent specific as described above may be employed instead of or in addition to plant material from the Euphorbia lathyrus Euphorbia lathyrus can be grown in a variety of climates and conditions with prolific harvests at relatively low costs and high yields in tonnage per acre. Euphorbia lathyrus has been produced from seed at selected Southern Oregon fields at the rate of 5-6 green tons, or 2-3 dry tons, per acre at a cost of approximately $300-500/acre. Seed grown Euphorbia yields a "second year" harvest, and seedlings may be planted instead to yield a crop in the first year. For seedlings the cost rises to approximately $600-800/acre.

Conventional harvesting, grinding or chopping, and pelletizing machinery are adequate in the handling and processing of Euphorbia lathyrus into pellets as long as precautions for worker safety and health are taken, such as full body covering protective garments and goggles and masks to keep airborne particulate caustic plant material out of the eyes, noses, and mouths of workers. Agricultural quality euphorbia seeds may be purchased in quantity from the Haas Gold Ring Seed Company, Yakima, WA, U.S.A.

Once in pelletized form, the Euphorbia lathyrus plant materials are extremely well suited for distribution in agricultural rodent infested settings by any of a number of well known pellet spreading methods in the industry. The rodenticidal quality of the Euphorbia lathyrus pellets does not deteriorate appreciably with the passage of time despite changes in weather conditions. Since agricultural crops are hardest hit in the lean winter months when rodent food supplies are scarce, the Euphorbia lathyrus pellets become an alternative or supplementary food source for the scavenging rodents. Rodents will still consume the toxic pellets during other seasons, though not so strongly as during winter.

The pelletized above ground Euphorbia lathyrus plant materials, and especially the pelletized ground seeds are highly toxic to rodents, as born out by limited preliminary testing, wherein ingestion of as little as three grams of pellet per typical adult laboratory rat caused disablement or death of the rodent. In other limited testing conducted in the Fall of the year, a test plot of ten by twenty foot ground known to be infested by mice, gophers, and moles was treated with Euphorbia pellets by placing approximately two tablespoons of pellets in each visible rodent hole, for a total of approximately one half pound of pellets over the test plot. Within 10 days, all evidence of rodent activity, including rodent sightings, had disappeared from the test plot with no evidence of pellet expulsion from the rodent holes. It is believed that this latter datum suggests that the pellets were consumed, as it is known the rodents will quickly expel inedible matter from their holes. Where Euphorbia lathyrus pellets are the only, or nearly the only, food source, further limited tests suggest that laboratory rats will consume sufficient quantities of the pellets to die within three to four days.

Although not essential, various ingredients may be added to the ground Euphorbia lathyrus plant material such as binders and attractants. The Euphorbia lathyrus plant materials pelletize remarkably well without the addition of binders but some applications and processes may benefit from the addition of some binder constituents. Similarly, it is contemplated that a percentage by weight of some conventional rodent attracting substance such as a conventional sweetener like molasses or one of the non-nutritive sweeteners as discussed in the Lazar reference cited above can be added to the ground materials or to the pellets themselves. The exact percentage will vary with the needs and desires of the end user.

Because of several important factors, most rodent infested crop areas and orchards do not lend themselves to the kind of conventional protection which home gardeners report they receive from planted hedges of Euphorbia lathyrus plants. First of all the large acreage typically involved with commercial crop growing areas and orchards make the planting of a hedge to surround that acreage costly and impractical and fraught with potential imperfections in the ring of protection such as are familiar to anyone in the art of establishing and maintaining a large defensive perimeter of any sort. Dividing the rodent affected area into smaller areas for effective hedging is impratical and also inconsistent with modern machine based agricultural methods of watering, hoeing, weeding, spraying, and the like.

As alluded to above, the rodenticidal pellets of Euphorbia lathyrus can be made either from the above ground portions of the Euphorbia lathyrus plants including the seeds, or from the plant materials alone after the seeds have first been removed, or simply from the ground-up seeds themselves, for maximum toxicity per pellet.

The composition of the invention is preferably produced by harvesting the above ground portions of a cultivated field of Euphorbia lathyrus with conventional above ground swather type crop harvesting machinery into conventional wind-rows. In one embodiment the seeds are removed from the harvested Euphorbia lathyrus plant material and either saved for seed sales or for separate grinding and pelletization. In another embodiment the plant materials, including the seeds, are simply chopped by conventional chopping machinery to a size range of approximately ¼"×¼" to ½"×½". It has been found that a conventional field chopper serves well to chop and prepare the Euphorbia lathyrus materials for pelletization.

In the embodiment in which the seeds are first extracted, the plant materials are then chopped as above described without the seeds. In a preferred embodiment no binding ingredients need be added to the chopped Euphorbia lathyrus plant material. However applications will occur to those skilled in the art wherein the addition of one or more conventional binder ingredients in small percentages by weight will appear to be beneficial. For example, the chopped seeds sometimes do not pelletize as readily, at a given pelletization output rate, as do the other chopped Euphorbia materials. While this may be remedied by running the pellet mill slower, which probably heats the pellets hotter, a binder might also be added. Similarly, it is not necessary that the Euphorbia lathyrus be the only constituent of the rodenticide pellet, except that toxicity per pellet will obviously decline in proportion to the percentage inclusion of other nontoxic ingredients.

Similarly in a preferred embodiment no attractant ingredients such as sweeteners are necessary because the plant materials themselves are sufficiently attractive to a rodent starved enough to be a serious threat to the exposed crop plants or trees. However the variety of applications in which the rodenticide may be employed, and the relative degree of attractiveness of the pelletized rodenticide, may be increased by any of several well known attractant methods such as inclusion of a small percentage of molasses or other known rodent attractant ingredients as described in the above cited references or some non-nutritive artificial sweetener such as that described above in the Lazar reference.

In a preferred embodiment the roughly cylindrical pellets are formed in a California Pellet Mill Century pelletization mill to a finished size of approximately 5/32" in diameter by ½" long. However pellet sizes may be varied depending upon the target rodent group. For instance smaller pellets will be more attractive to smaller rodents.

In a preferred method for distributing these pellets in fruit orchards, the pellets are evenly distributed along the tree rows and on the orchard ground around the trees and roots at that time of year when other common rodent food sources have begun to dwindle. However distribution may be made at other times of the year as well. This particular time of year will vary depending upon the climate, locale, type of target rodents, and type of crops, as will be appreciated by those skilled in the art. It appears that rodents will not attack the orchard trees until other more accessible and more preferable forms of rodent food have dwindled At this time of year the pellets are spread by hand, or where appropriate, by a conventional piece of pellet spreading machinery. Pellets are typically spread before there is a winter ground covering such as snow or ice, but the damage inflicting rodents will forage out the covered pellets through such a ground covering. The control of the rodents is effected when the rodents eat the pellets because they are more available and more attractive, and then die from eating the pellets.

Other forms of distribution of the rodenticide pellets will be more applicable to other types of crop distributions. However in general a directed form of distribution is preferred as opposed to a general or uniform acreage kind of distribution for reasons of cost effectiveness. Thus the rodenticide pellets are usually directed to the area amidst the crops where the damage is expected to occur and the precise placement of the pellets will depend upon the crops planted.

In compliance with the statute, the invention has been described in language more or less specific as to its features. It is to be understood, however, that the invention is not limited to the specific features shown, since the means and composition disclosed comprise preferred forms of putting the invention into effect. The invention is, therefore, claimed in any of its forms or modifications within the legitimate and valid scope of the appended claims, appropriately interpreted in accordance with the doctrine of equivalents.

INDUSTRIAL APPLICABILITY

This rodenticide will find wide spread use in the agricultural industry particularly where large fields of crops or orchards are grown which are attractive to rodents, such as fruit orchards. Even where other rodenticides might also be employed, the rodenticide of the invention is highly effective in controlling rodents and extremely cost effective as well. It is to be noted that the toxic agent for the rodents is a caustic substance which is also in some measure toxic to humans and other animals. Therefore care must be taken in handling the rodenticide to avoid contact with human tissue, both during the manufacturing and the distribution of the rodenticide.

I claim:

1. A distributable rodenticide comprised of pelletized Euphorbia lathyrus plant materials.

2. The rodenticide of claim 1 comprised of the seed portion only of the Euphorbia lathyrus plant.

3. A distributable rodenticide comprising chopped portions of the Euphorbia lathyrus plant and an added sweetener.

4. The rodenticide of claim 1 comprised of at least 85% by weight chopped plant materials from Euphorbia lathyrus.

5. The rodenticide of claim 4 where only above ground portions of Euphorbia lathyrus are chopped as constituents of said rodenticide.

6. The rodenticide of claim 4 wherein the composition by weight of Euphorbia lathyrus is 95% or greater.

7. The rodenticide of claim 4 further comprising an inert pelletizing binder of no greater composition by weight than 5%.

8. The rodenticide of claim 4 further comprising an added sweetener.

* * * * *